(12) United States Patent
Arima (10) Patent No.: US 9,313,868 B2
(45) Date of Patent: Apr. 12, 2016

(54) RADIOGRAPHY CONTROL APPARATUS AND RADIOGRAPHY CONTROL METHOD

(71) Applicant: CANON KABUSHIKI KAISHA, Tokyo (JP)

(72) Inventor: Keisuke Arima, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 331 days.

(21) Appl. No.: 13/915,365

(22) Filed: Jun. 11, 2013

(65) Prior Publication Data
US 2013/0336457 A1 Dec. 19, 2013

(30) Foreign Application Priority Data
Jun. 15, 2012 (JP) ................. 2012-135830

(51) Int. Cl.
*H05G 1/30* (2006.01)
*A61B 6/00* (2006.01)

(52) U.S. Cl.
CPC *H05G 1/30* (2013.01); *A61B 6/465* (2013.01); *A61B 6/563* (2013.01); *A61B 6/4266* (2013.01); *A61B 6/545* (2013.01)

(58) Field of Classification Search
CPC .... A61B 6/4405; A61B 6/566; A61B 6/4266; A61B 6/465; A61B 6/545; A61B 6/563; G06F 19/321; G06F 19/3418; H05G 1/30
See application file for complete search history.

(56) References Cited

U.S. PATENT DOCUMENTS

2006/0242552 A1* 10/2006 Tanaka ................. 715/500.1

FOREIGN PATENT DOCUMENTS

JP 200681761 A 3/2006

* cited by examiner

*Primary Examiner* — Irakli Kiknadze
(74) *Attorney, Agent, or Firm* — Canon USA Inc. IP Division (57) ABSTRACT

A radiography control apparatus according to the present invention includes an examination order acquiring unit configured to acquire an examination order through a network, a search condition specifying unit configured to specify a search condition for acquiring the examination order, and an imaging preparation unit configured to perform imaging preparation processing in a case where a result of the acquisition by the examination order acquiring unit satisfies an imaging start condition.

11 Claims, 8 Drawing Sheets

| PATIENT NAME: | | |
|---|---|---|
| PATIENT ID: | | |
| EXAMINATION ID: | | |
| EXAMINATION DATE AND TIME: | y/M/d h:mm ~ y/M/d h:mm | |
| | CANCEL | EXAMINATION ACQUISITION |

IMAGING METHOD LIST

| SKULL FRONT SENSOR A | SKULL SIDE SENSOR A | NASAL BONE SIDE SENSOR A |
| CERVICAL VERTEBRAE FRONT SENSOR A | CERVICAL VERTEBRAE SIDE SENSOR A | CHEST FRONT SENSOR A |
| CHEST SIDE SENSOR A | CHEST FRONT SENSOR B | CHEST SIDE SENSOR B |
| CHEST FRONT SENSOR C | CHEST SIDE SENSOR C | THORACIC VERTEBRAE FRONT SENSOR B |
| THORACIC VERTEBRAE SIDE SENSOR B | PEDIATRIC CHEST FRONT SENSOR C | PEDIATRIC CHEST SIDE SENSOR C |
| NEONATAL CHEST FRONT SENSOR D | NEONATAL CHEST SIDE SENSOR D | CHEST FRONT SENSOR A |
| ABDOMEN SIDE SENSOR A | ABDOMEN FRONT SENSOR C | ABDOMEN SIDE SENSOR C |
| PELVIS FRONT SENSOR A | PELVIS SIDE SENSOR A | PELVIS FRONT SENSOR B |

PATIENT NAME: AAA AAA
PATIENT ID: P111
BIRTH DATE: 2001/1/10
AGE: 8
SEX: MALE

EXAMINATION ID: O003

| CHEST FRONT SENSOR A |
| CHEST SIDE SENSOR A |

IMAGING INFORMATION INPUT

EXAMINATION START

FIG. 6

RADIOGRAPHY CONTROL APPARATUS AND RADIOGRAPHY CONTROL METHOD

BACKGROUND OF THE INVENTION

1. Field of the Invention

The present invention relates to a radiography control apparatus and a radiography control method for sending and receiving an X-ray image.

2. Description of the Related Art

In recent years, hospital information systems through network connection have been created for hospitals. For example, when it is determined that X-ray imaging is necessary, an instruction for an examination is input into a hospital information system (HIS) terminal to be transmitted to a radiology department, which is a receiver of the request.

This request information is referred to as examination order. An examination order includes a department name of an originator of the request, an examination item, and personal data of a patient. Upon receiving an examination order in a radiology information system (RIS), the radiology department adds an imaging condition and the like to the order and transfers the order to an X-ray examination system. The X-ray examination system performs the X-ray imaging in accordance with the examination order that has been received. A captured image is added to examination information for transfer to a picture archiving and communication systems (PACS) and for printing. In some cases, a search condition, such as a patient ID and an examination time, is specified in the X-ray examination system to receive an examination order.

In an approach disclosed in Japanese Patent Application Laid-Open No. 2006-81761, a user sets search conditions such as a patient ID and an examination time to display a list of examination orders that match the search conditions. This approach presents a challenge, in terms of user convenience, in that the user is required to provide an instruction for selection even with a single examination result.

SUMMARY OF THE INVENTION

The present invention has been achieved in light of the challenge described above. An object of the present invention is to facilitate performing of an examination with a reduced risk of patient misidentification and the like.

To solve the challenge described above, a radiography system according to the present invention has been achieved in light of the challenge described above and includes: an examination order acquiring unit configured to acquire an examination order through a network; a search condition specifying unit configured to specify a search condition for acquiring the examination order; and an imaging preparation unit configured to perform imaging preparation processing in a case where a result of the acquisition by the examination order acquiring unit satisfies an imaging start condition.

Further features of the present invention will become apparent from the following description of exemplary embodiments (with reference to the attached drawings).

DESCRIPTION OF THE EMBODIMENTS

Some embodiments of the present invention will be described hereinafter in detail with reference to the drawings. In the embodiments described herein, an exemplary case using X-rays as radiation rays will be described. The radiation rays, however, are not limited to X-rays and may be, for example, electromagnetic waves, α-rays, β-rays, and γ-rays.

First Embodiment

Figure 1:
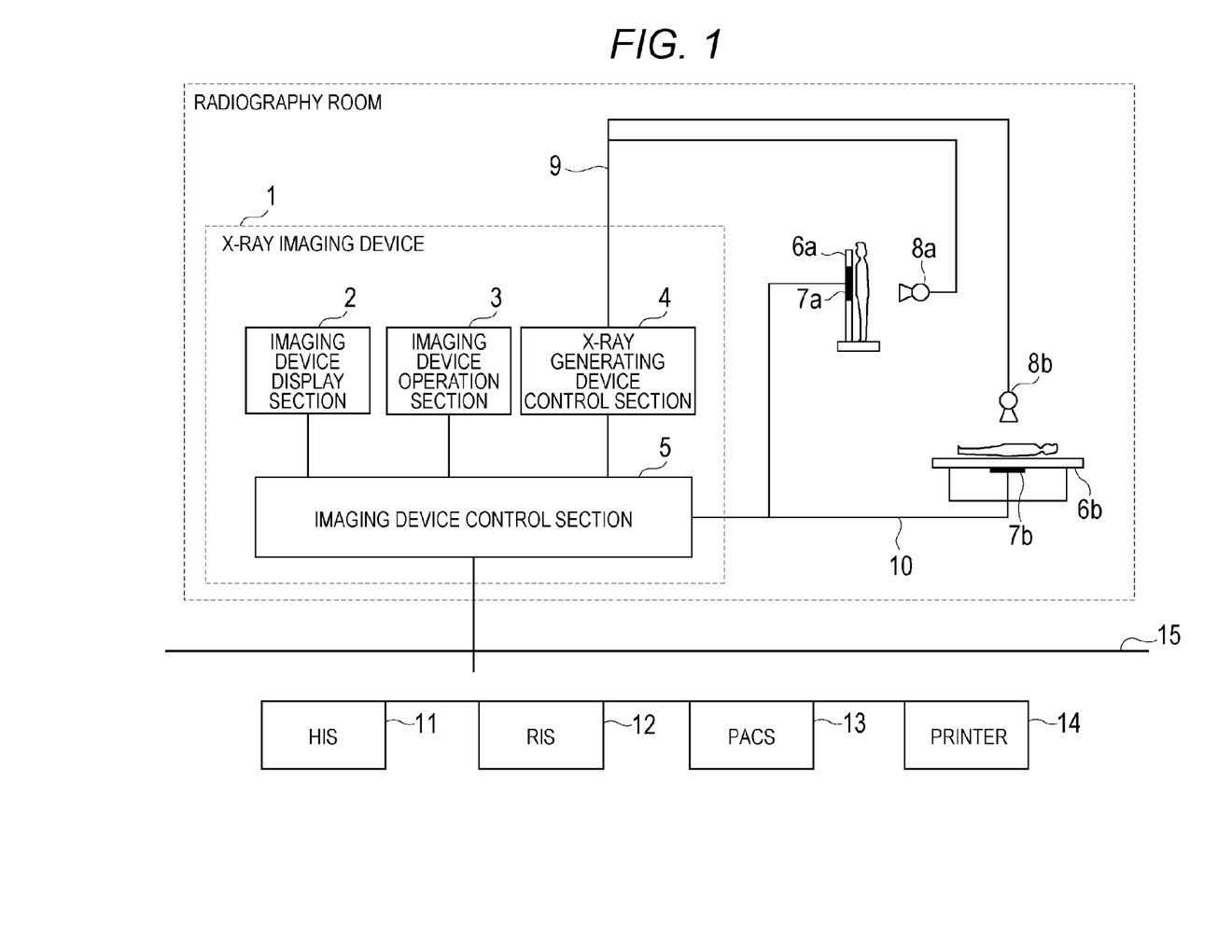
FIG. 1 is a block diagram of a medical examination system according to the present embodiments.

FIG. 1 is a diagram of an exemplary configuration of a radiography system (hereinafter referred to as X-ray imaging system) according to an embodiment of the present invention.

In the X-ray imaging system, an X-ray imaging device 1, a radiology information system (RIS) 12, a PACS (image server) 13, and an HIS (hospital information system) 11 are connected. These devices are connected through a communication unit 15 including a local area network (LAN) and a wide area network (WAN). These devices each include one or a plurality of computers. Each computer includes a main control unit, such as a CPU, and a storing unit, such as a read only memory (ROM) and a random access memory (RAM). Each computer may also include a communication unit, such as a network card, and an input/output unit, such as a keyboard, a display, and a touch panel. These units are connected through a bus or the like, and are controlled by execution, by the main control unit, of a program stored in the storing unit.

The X-ray imaging device 1 includes an imaging device display section 2, an imaging device operation section 3, an imaging device control section 5, and an X-ray generating device control section 4.

The X-ray generating device control section 4 is connected through a cable 9 to an X-ray generation section in order to control X-ray emission from the X-ray generation section 8. Here, the X-ray generation section 8 (8a, 8b) functions as a radiation ray generation section. The X-ray generation section 8 is achieved by, for example, an X-ray tube and emits X-rays toward a subject (for example, a specific region of a patient).

The imaging device operation section 3 provides centralized control over processing in the X-ray imaging device 1. The imaging device display section 2 is achieved by, for example, a liquid crystal display and displays various types of information for an operator (for example, a radiographer and a doctor). The imaging device operation section 3 is achieved by, for example, a mouse and an operation button and allows the operator to input various instructions into the device. Note that, alternatively, the imaging device display section 2 and the imaging device operation section 3 may be achieved by a touch panel that combines the imaging device display section 2 and the imaging device operation section 3.

The X-ray imaging device 1 is connected through a cable 10 to an X-ray detector 7 (7a, 7b), such that electrical power, an image signal, a control signal, and the like are given and received by the X-ray imaging device 1 and the X-ray detector 7 through the cable 10.

The X-ray detector 7 functions as a detector to detect X-rays transmitted through the subject and to acquire an X-ray image (a radiation ray image) based on the subject. In other words, the X-ray generation section 8 and the X-ray detector 7 operate in a coordinated manner to achieve an X-ray imaging section. Here, the X-ray detector 7 is installed on an imaging table 6 (6a, 6b) in a standing position and a lying position.

An exemplary configuration of the X-ray imaging system has been described. It should be noted that the configuration illustrated in FIG. 1 is just an example, and may be changed as appropriate. For example, in FIG. 1, the X-ray imaging device 1 is connected to the various devices through the communication unit 15, but the X-ray imaging device 1 does not have to be connected to such devices.

A processing sequence of the X-ray imaging system illustrated in FIG. 1 for capturing an X-ray image will now be described in a sequence of an examination.

Figure 2:
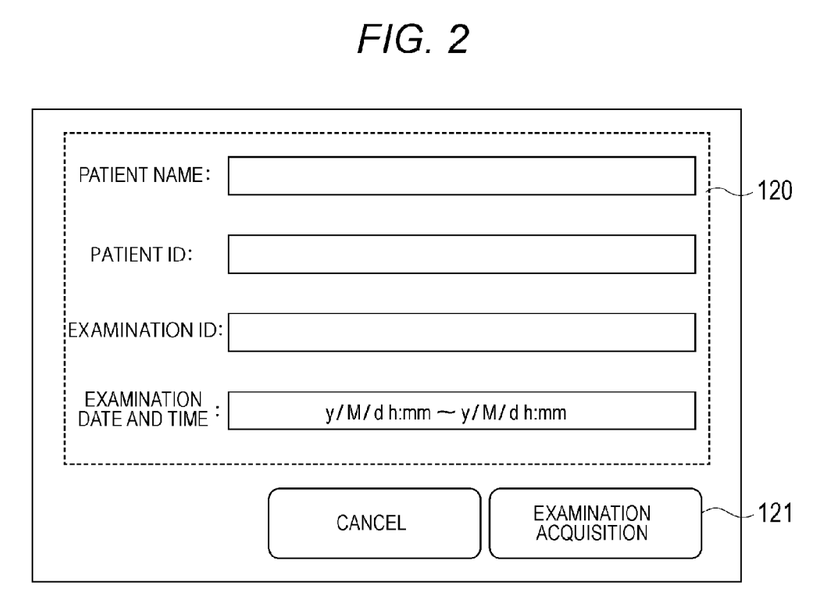
FIG. 2 is a diagram of an exemplary search condition input screen.

The X-ray imaging device 1 allows the imaging device display section 2 to display a search condition input screen illustrated in FIG. 2. The search condition input screen includes a patient/examination information input section 120, an examination acquisition button 121, and a cancel button, as illustrate in FIG. 2.

For acquiring an examination from the RIS, patient information (a patient name, a patient ID, and the like) and examination information (an examination ID, examination date and time, and the like) for the examination to be performed are input into the patient/examination information input section 120. Once the information is input and, then, the examination acquisition button 121 is pressed, the X-ray imaging device notifies, through the network, the RIS 12 of an examination acquisition request including a search condition that has been input from the search condition input screen. Upon receiving the examination acquisition request, the RIS 12 returns to the X-ray imaging device 1 an examination that matches the search condition.

Figure 3A:
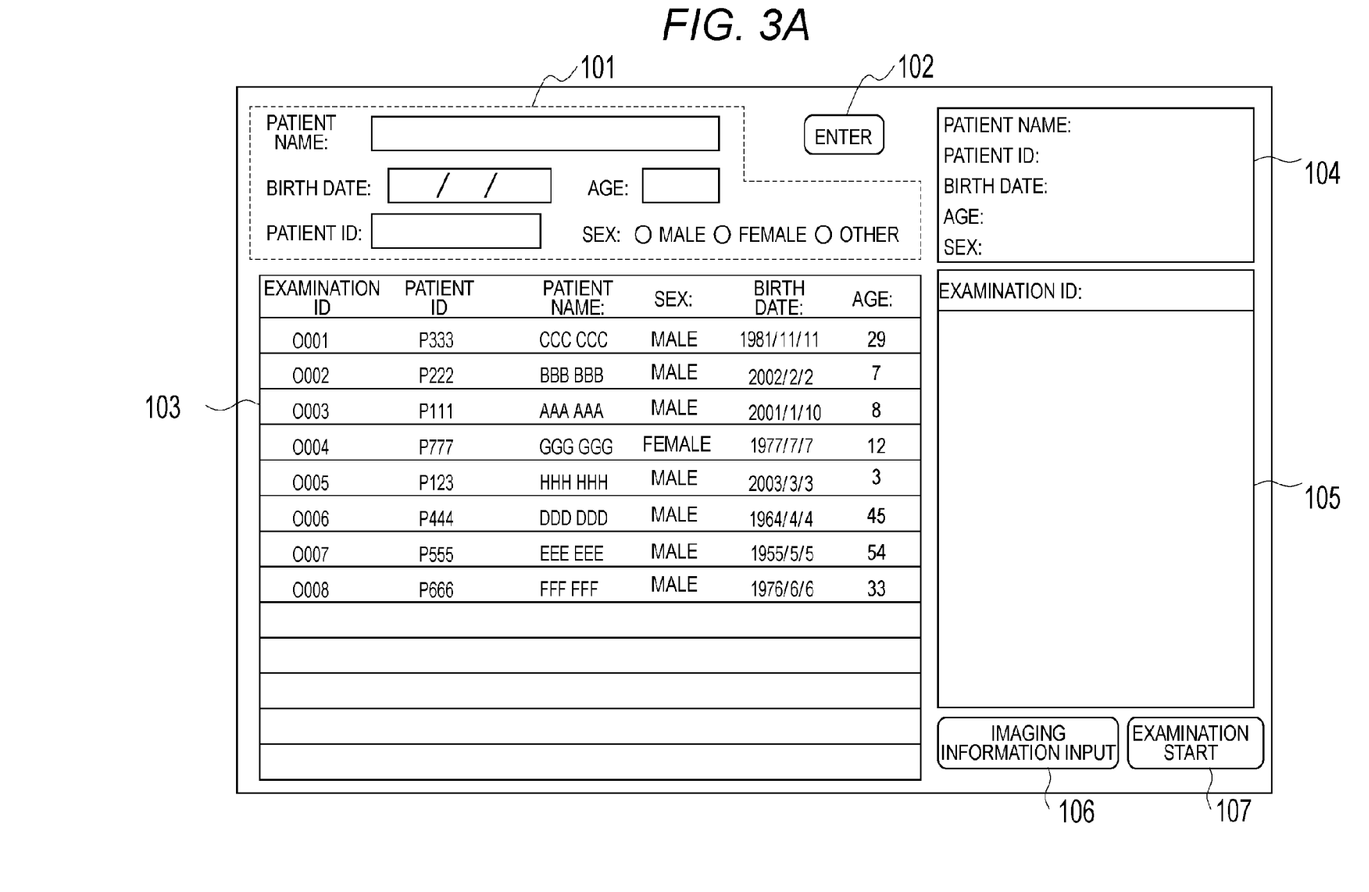
FIG. 3A is a diagram of an exemplary new examination input screen.
Figure 3B:
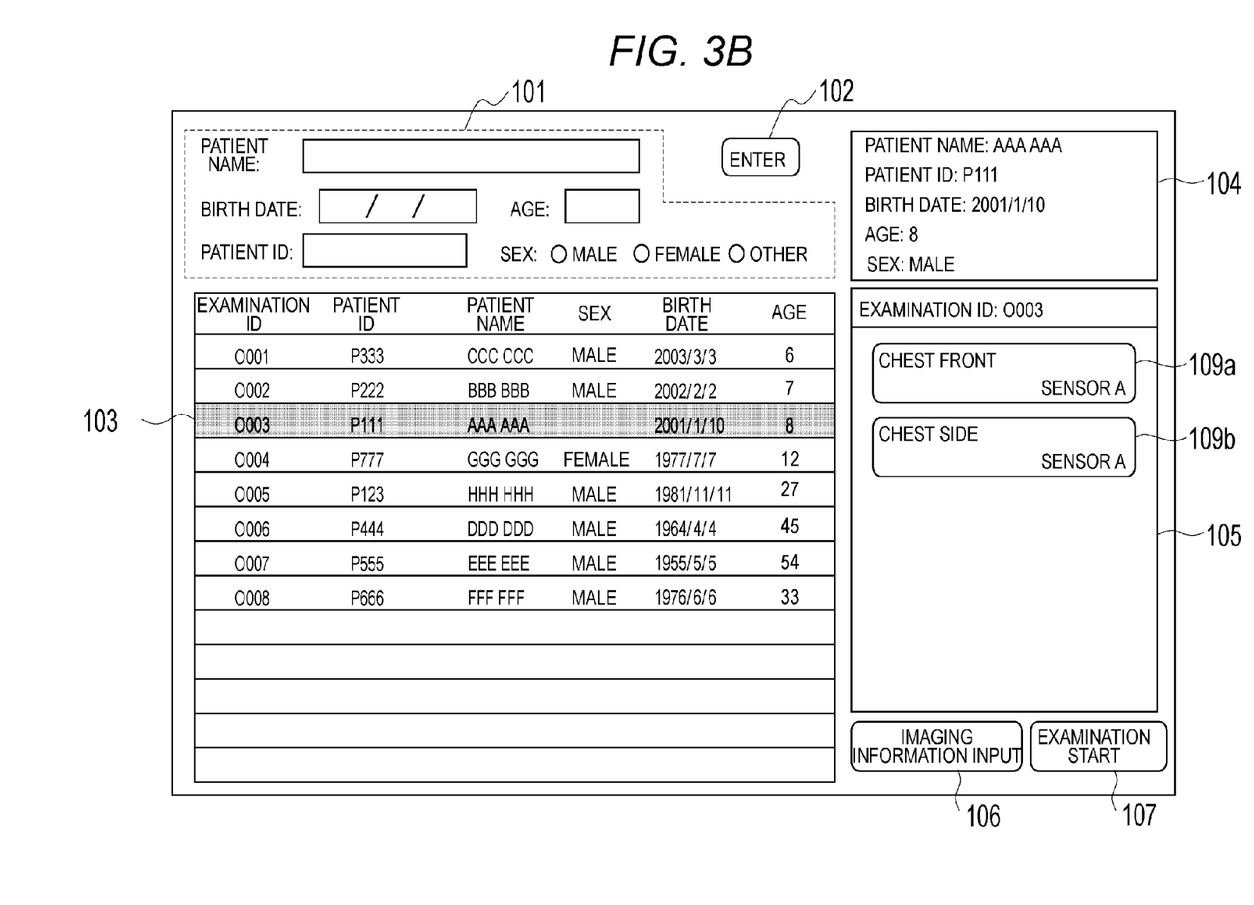
FIG. 3B is a diagram of an exemplary new examination input screen.
Figure 3C:
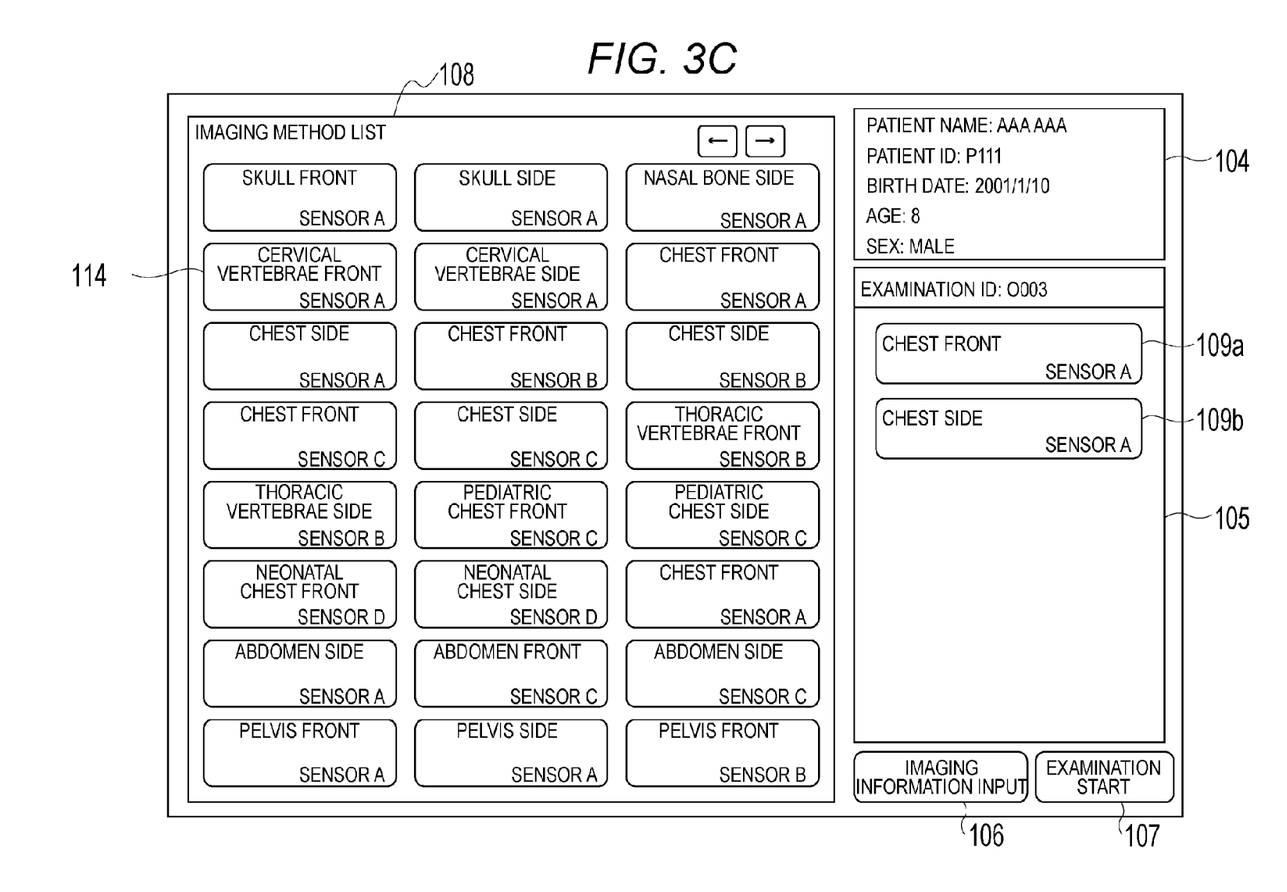
FIG. 3C is a diagram of an exemplary new examination input screen.

The X-ray imaging device 1, having acquired the examination from the RIS 12, allows the imaging device display section 2 to display a new examination input screen illustrated in FIGS. 3A to 3C. As illustrated in FIG. 3A, the new examination input screen includes a patient information input area 101, a patient information enter button 102, a requested-examination list 103, a patient information display area 104, an imaging information display area 105, an imaging information input button 106, and an examination start button 107.

In the requested-examination list 103, the examination acquired from the RIS 12 is displayed in a list form. When any examination from the requested-examination list 103 is selected, patient information (a patient ID, a patient name, a birth date, and the like) corresponding to a selected patient is displayed in the patient information display area 104 as illustrated in FIG. 3B. In the imaging information display area 105, an examination ID is displayed, and in an area directly below the examination ID, imaging information corresponding to the examination ID is displayed. The imaging information is received from the RIS 12 as described above. In a case with FIG. 3B, an imaging method button 109 (a chest front button 109a, a chest side button 109b) corresponding to the imaging information is positioned. Upon pressing of the imaging information input button 106, an imaging information input area is displayed as illustrated in FIG. 3C to allow addition of a further imaging method.

The operator checks the patient information and the imaging information and, then, presses the examination start button 107. This determines the examination to be performed.

Figure 4:
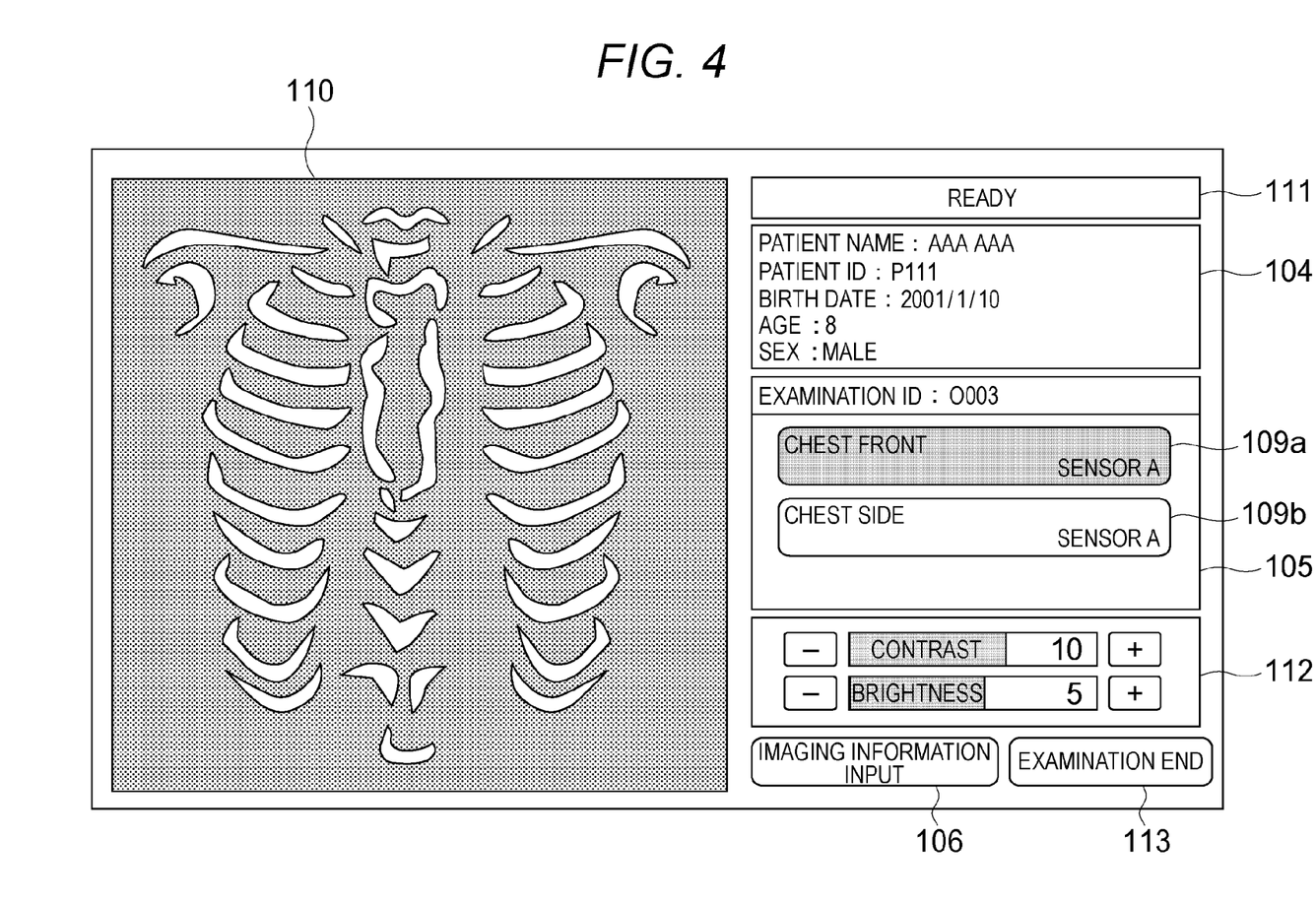
FIG. 4 is a diagram of an exemplary imaging screen.

Following the pressing of the examination start button 107, the X-ray imaging device 1 allows the imaging device display section 2 to display an imaging screen illustrated in FIG. 4. The imaging screen is a screen used for imaging.

The imaging screen basically includes display areas similar to those of the new examination input screen described with reference to FIGS. 3A to 3C. As additional display areas, an image display area 110, a message area 111, an image processing setting area 112, and an examination end button 113 are included as illustrated in FIG. 4.

In the imaging screen, when displayed, the imaging method button 109a, positioned uppermost in the imaging information display area 105, is selected by default. Following this, the X-ray imaging device 1 allows the imaging device control section 5 to send to the X-ray generating device control section 4 an imaging condition (a tube voltage, a tube current, an irradiation time, and the like) set in correspondence with the imaging method button (that is, an imaging method thereof). Then, the imaging device control section 5 controls the X-ray detector 7 in accordance with the imaging condition in preparation for imaging.

When the preparation is completed, the X-ray imaging device 1 achieves a transition to a state in which imaging is possible. The message area 111, then, displays a "Ready message" to indicate the state in which the imaging is possible.

Subsequently, the operator checks the imaging method, performs setting of the imaging, and positions the patient. When a series of imaging preparations is completed, the operator references the message area 111 to confirm that the state in which the imaging is possible is indicated, and presses an X-ray emission switch (not shown). Then, the X-ray imaging device 1 allows the X-ray generation section 8 to emit X-rays toward a subject (a specific region of the patient), and allows the X-ray detector 7 to detect X-rays that have transmitted through the subject. This enables an X-ray image to be captured.

Once the imaging is finished, the X-ray imaging device 1 allows the imaging device control section 5 to acquire the captured image from the X-ray detector 7. The X-ray imaging device 1 also performs image processing on the captured and acquired image in accordance with a predetermined image processing condition. The predetermined image processing condition is defined in advance in correspondence with the imaging method.

When the image processing is finished, the X-ray imaging device 1 allows the captured image display area 110 to display the captured image that has been subjected to the image processing. In a case where it is desired that, for example, contrast of the captured image be changed, the operator operates a button for contrast, brightness, or the like provided in the image processing setting area 112. This allows the operator to perform additional image processing on the captured image displayed in the captured image display area 110. Here, if the operator presses the imaging method button 109 for which imaging has not been performed, the imaging condition and the image processing condition for the image are saved, and then subsequent imaging will start.

The operator repeats the procedure described above to perform imaging for all imaging methods in the imaging information display area 105. When the entire imaging is finished, the operator presses the examination end button 113. This completes a series of examinations, and the X-ray imaging device 1 again displays the search condition input screen. At this point in time, the X-ray imaging device 1 allows the imaging device control section 5 to output the captured image, the examination information, and the like to, for example, the PACS 13, a printer (not shown), the RIS 12, and a ROM within the X-ray imaging device 1. Note that in the RIS 12, the ROM, and the like, the captured image and the patient information are associated with each other and stored.

An operation of the X-ray imaging system according to the present embodiment will now be described with reference to a flowchart illustrated in FIG. 5.

Figure 5:
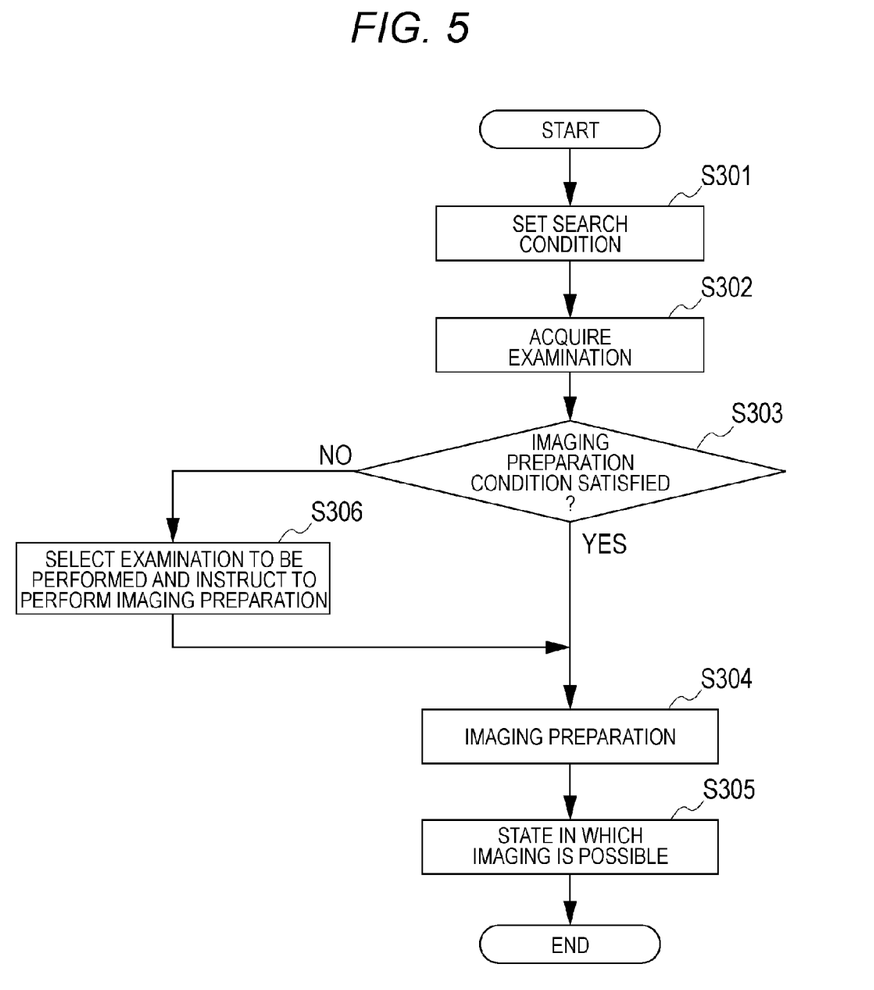
FIG. 5 is a flowchart according to a first embodiment.

With reference to FIG. 5, in step S301, a search condition for an examination to be acquired is input. In step S302, an examination that matches the search condition specified in step S301 is acquired from the RIS.

In step S303, whether the examination acquired from the RIS 12 matches an imaging preparation condition is confirmed. Here, the imaging preparation condition is a condition to confirm that there is one examination option to start with. The condition may be "that there is one examination that has been acquired." If it is possible to perform more than one examination for an identical patient, the condition may be "that all examinations that have been acquired are for an identical patient."

If the imaging preparation condition is satisfied, imaging preparation is performed in step S304. The imaging preparation includes the display of the imaging screen, the drive control of the X-ray detector 7, and the notification of the imaging condition to an X-ray generating device.

When the imaging preparation described above is completely finished, the state in which imaging is possible is achieved in step S305.

If the imaging preparation condition is not satisfied in step S303, then in step S306, an examination to be performed is selected from the requested-examination list, and an instruction to start the examination is issued to perform the imaging preparation.

As described above, according to a first embodiment, by setting a search condition such that the imaging preparation condition is satisfied, an operation to select an examination from the requested-examination list and an operation to issue an instruction to start the examination are eliminated. In addition, the preparation to start the examination is automatically performed to achieve a transition to the state in which the imaging is possible, facilitating performing of an examination.

As a unit for acquiring an examination, an example where communication with the RIS 12 is allowed through a network has been described. Alternatively, a method for acquiring an examination not through a network, for example, by input with a file, may be used. In addition, as a unit for searching, a unit for narrowing down the requested-examination list may be provided using, for example, a search field and a bar code reader, and the imaging preparation condition may be applied to a result of the narrowing down.

Second Embodiment

A second embodiment will now be described. As drive modes of an X-ray detector 7, an imaging mode and a standby mode, for example, are available. The imaging mode is a mode in which a voltage is applied to an image sensor so that an X-ray image can be acquired once X-rays are emitted. The standby mode is a mode in which a voltage application to the image sensor is stopped. In the present embodiment, a case will be described with reference to a flowchart illustrated in FIG. 6, in which the drive control of the X-ray detector 7 is performed in accordance with a result of the examination acquisition, so that a transition time to the state in which imaging is possible is reduced.

Figure 6:
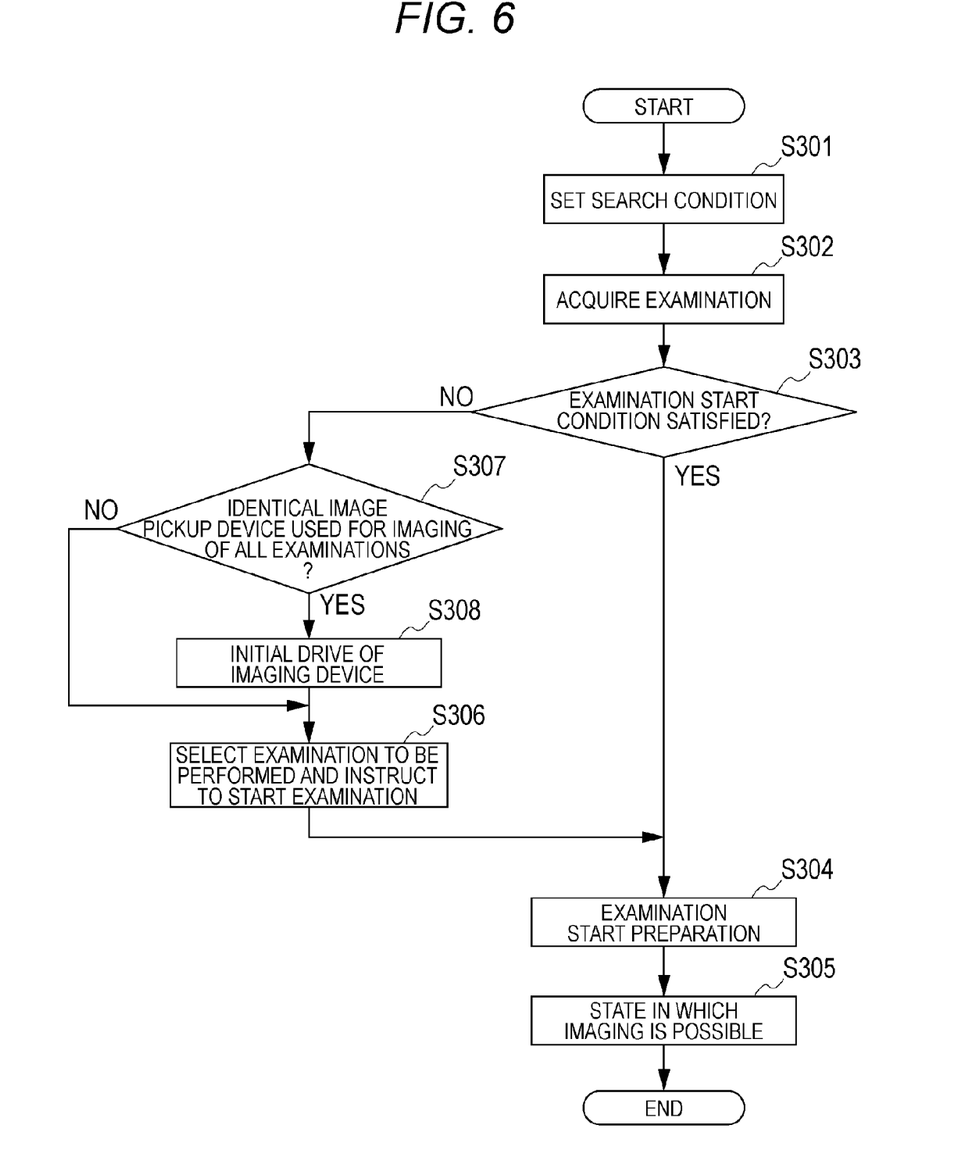
FIG. 6 is a flowchart according to a second embodiment.

Steps S301, S302, and S303 are similar to the first embodiment, and, thus, the description thereof will not be repeated.

If the imaging preparation condition is not satisfied in step S303, whether the identical X-ray detector is used for imaging of all acquired examinations is confirmed in step S307. It is contemplated that a plurality of X-ray detectors is used for an examination, and, hence, the determination may be on the basis of whether the identical X-ray detector 7 is used for a beginning of the imaging of all acquired examinations.

If the identical X-ray detector 7 is used for all acquired examinations, an emission enabling signal (a driving signal) is sent to the X-ray detector 7 in step S308. Following this, the X-ray detector 7 applies a voltage to the image sensor and starts shifting to the imaging mode described above.

Then, in step S306, an examination to be performed is selected from the requested-examination list, and an instruction to start the examination is issued.

In this case, the drive control, which has been performed in step S308 on the X-ray detector 7 to the imaging mode, is skipped to simplify the imaging preparation in step S304. It should be noted that the procedures of the radiography control achieved in the first embodiment and the second embodiment described above may be performed by a computer that reads a computer program recorded in a computer readable recording medium and that functions as a radiography control apparatus.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-135830, filed Jun. 15, 2012, which is hereby incorporated by reference herein in its entirety.

What is claimed is:

1. A radiography control apparatus, comprising:
a search condition specifying unit configured to specify a search condition for acquiring an examination order;
an examination order acquiring unit configured to acquire the examination order based on the search condition through a network; and
an imaging preparation unit configured to determine whether the examination order acquired by the examination order acquiring unit corresponds to an imaging start condition or not, and shift an X-ray detector to an imaging mode in a case where the examination order corresponds to the imaging start condition.

2. The radiography control apparatus according to claim 1, wherein the imaging start condition is that there is one examination order that has been acquired.

3. The radiography control apparatus according to claim 1, wherein the imaging start condition is that examination orders that have been acquired are for an identical patient.

4. The radiography control apparatus according to claim 1, wherein the imaging start condition is that an identical image pickup device is used for imaging methods designated for all examination orders that have been acquired.

5. The radiography control apparatus according to claim 1, further comprising an imaging screen for performing imaging in accordance with the examination order,
wherein the imaging preparation unit switches a screen display to the imaging screen as the imaging preparation processing.

6. The radiography control apparatus according to claim 1, wherein
an imaging method is designated for the examination order, and
the imaging preparation unit starts an initial drive of a detector to be used for the imaging method, so that a transition to a radiation ray accumulation standby state is achieved.

7. The radiography control apparatus according to claim 1, further comprising an imaging condition notification unit configured to notify a radiation ray generating device of an imaging condition,
wherein the imaging preparation unit allows the imaging condition notification unit to notify the radiation ray generating device of an imaging condition for an imaging method defined by the examination order.

8. The radiography control apparatus according to claim 1, further comprising a display control unit configured to allow a display unit to display an examination order selection screen for an operator to select an examination order in a case where the result of the acquisition by the examination order acquiring unit does not satisfy the imaging start condition.

9. The radiography control apparatus according to claim 8, wherein, even when the result of the acquisition by the examination order acquiring unit does not satisfy the imaging start condition, the imaging preparation unit performs the imaging preparation processing in a case where an identical image pickup device is to be used for imaging for imaging methods designated for all examination orders that have been acquired.

10. A radiography control method, comprising:
specifying, by a search condition specifying unit, a search condition for acquiring an examination order;
acquiring, by an examination order acquiring unit, an examination order based on the search condition through a network; and
determining, by an imaging preparation unit, whether the examination order acquired by the examination order acquiring unit corresponds to an imaging start condition or not, and shift an X-ray detector to an imaging mode in a case where the examination order corresponds to the imaging start condition.

11. A non-transitory computer readable recording medium storing a program for enabling a computer to perform control operations of a radiography control apparatus, comprising:
specifying a search condition for acquiring an examination order;
acquiring the examination order based on the search condition through a networks; and
determining whether the examination order acquired by the acquiring corresponds to an imaging start condition or not, and shift an X-ray detector to an imaging mode in a case where the examination order corresponds to the imaging start condition.

* * * * *